US00PP37262P2

(12) United States Plant Patent
Ammerlaan

(10) Patent No.: US PP37,262 P2
(45) Date of Patent: Feb. 10, 2026

(54) ***ARISTERIA* PLANT NAMED 'OVROCKS13'**

(50) Latin Name: x*Aristeria beguinii*
Varietal Denomination: OVROCKS13

(71) Applicant: Ovata B.V., Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 18 days.

(21) Appl. No.: 18/831,536

(22) Filed: Apr. 4, 2025

(30) Foreign Application Priority Data

Nov. 21, 2024 (QZ) ..... PBR 2024/2734

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
CPC ..... A01H 5/12; A01H 5/00; A01H 6/00
See application file for complete search history.

(56) References Cited

U.S. PATENT DOCUMENTS

PP30,905 P2 * 9/2019 Jachertz ..... A01H 6/00
Plt./373

* cited by examiner

*Primary Examiner* — June Hwu
(74) *Attorney, Agent, or Firm* — Samuel R. McCoy, Jr.

(57) ABSTRACT

A new and distinct x*Aristeria* beguinii cultivar named 'OVROCKS13' which is characterized by erect, inward-facing foliage that is arranged in a compact basal rosette, with foliage in the innermost whorls held very tightly. The thick lanceolate foliage exhibits a narrow acute to soft mucronate apex, green to yellow general coloration, and is densely covered with prominent greyed-green protuberances, with spines along the margins and top of the foliage. Protuberances on the leaf surface are arranged in distinct transverse rows. The new variety has shown to be uniform and stable in the resulting generations from asexual propagation.

4 Drawing Sheets

Latin name of the genus and species: The Latin name of the genus and species of the novel variety disclosed herein is x*Aristeria beguinii.*

Variety denomination: The inventive variety of *Aristeria* disclosed herein has been given the variety denomination 'OVROCKS13'.

CROSS REFERENCE TO RELATED APPLICATIONS

This application claims priority to the Community Plant Variety Rights application number 2024/2734, filed Nov. 21, 2024, which is herein incorporated by reference.

BACKGROUND OF THE INVENTION

Parentage: 'OVROCKS13' originated as a naturally occurring, whole-plant mutation of an unnamed x*Aristeria beguinii* (not patented). In 2018, the inventor discovered the mutation at a commercial greenhouse in Bleiswijk, the Netherlands, growing amongst a cultivated population of the species x*Aristeria beguinii*. The mutation was noted for its erect compact foliage and prominent greyed-green protuberances and was subsequently isolated for further evaluation in order to confirm the distinctness and stability of the characteristics first observed. Upon confirmation of distinctness and stability, 'OVROCKS13' was selected for commercialization in 2019.

Asexual Reproduction: Asexual reproduction of the new cultivar 'OVROCKS13', by way of rooting leaf cuttings, was first initiated in 2019 at the inventor's commercial greenhouse in Bleiswijk, the Netherlands. Through several subsequent generations, the unique features of this cultivar have proven to be stable and true to type.

SUMMARY OF THE INVENTION

The cultivar 'OVROCKS13' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'OVROCKS13'. These characteristics in combination distinguish 'OVROCKS13' as a new and distinct x *Aristeria beguinii* cultivar:

1. 'OVROCKS13' exhibits erect to slightly inward-facing foliage arranged in a compact basal rosette, with foliage in the innermost whorls held together very tightly; and
2. 'OVROCKS13' exhibits thick lanceolate leaves with a narrow acute to soft mucronate apex; and
3. 'OVROCKS13' exhibits green to yellow-green foliage that is densely covered with prominent greyed-green protuberances on both the adaxial and abaxial surfaces; and
4. 'OVROCKS13' exhibits foliage with serrulate to dentate margins and apices; and
5. 'OVROCKS13' exhibits protuberances which are arranged in distinct transverse rows and bearing spines in a distinct longitudinal row along the midrib.

BOTANICAL DESCRIPTION OF THE PLANT

Figure 1:
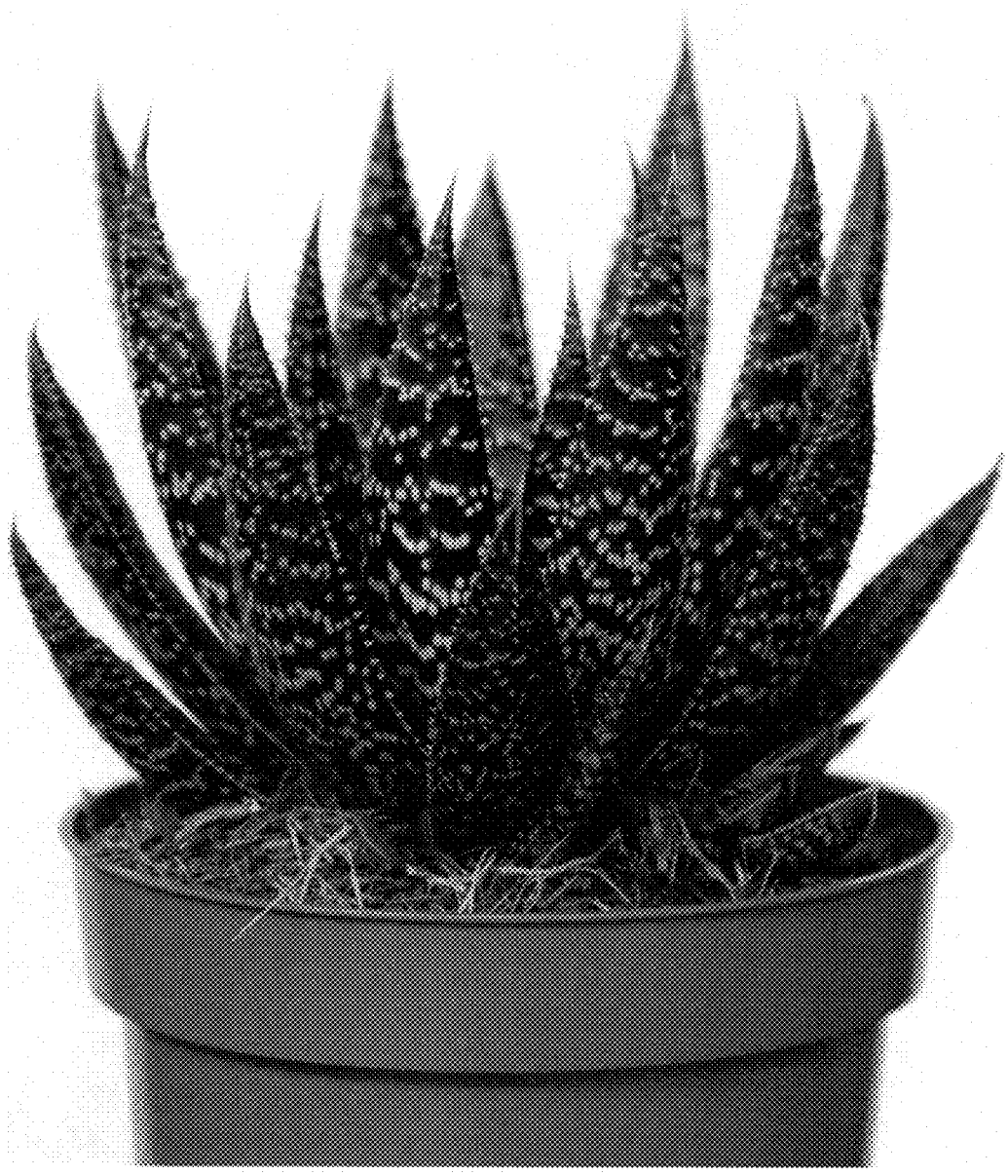
FIG. 1 illustrates, as nearly true as it is reasonably possible to make the same in color photographs of this type, an exemplary plant of 'OVROCKS13' grown in a commercial greenhouse in Heerhugowaard, the Netherlands. This plant is approximately 18 months old, planted in a 12 cm container.
Figure 2:
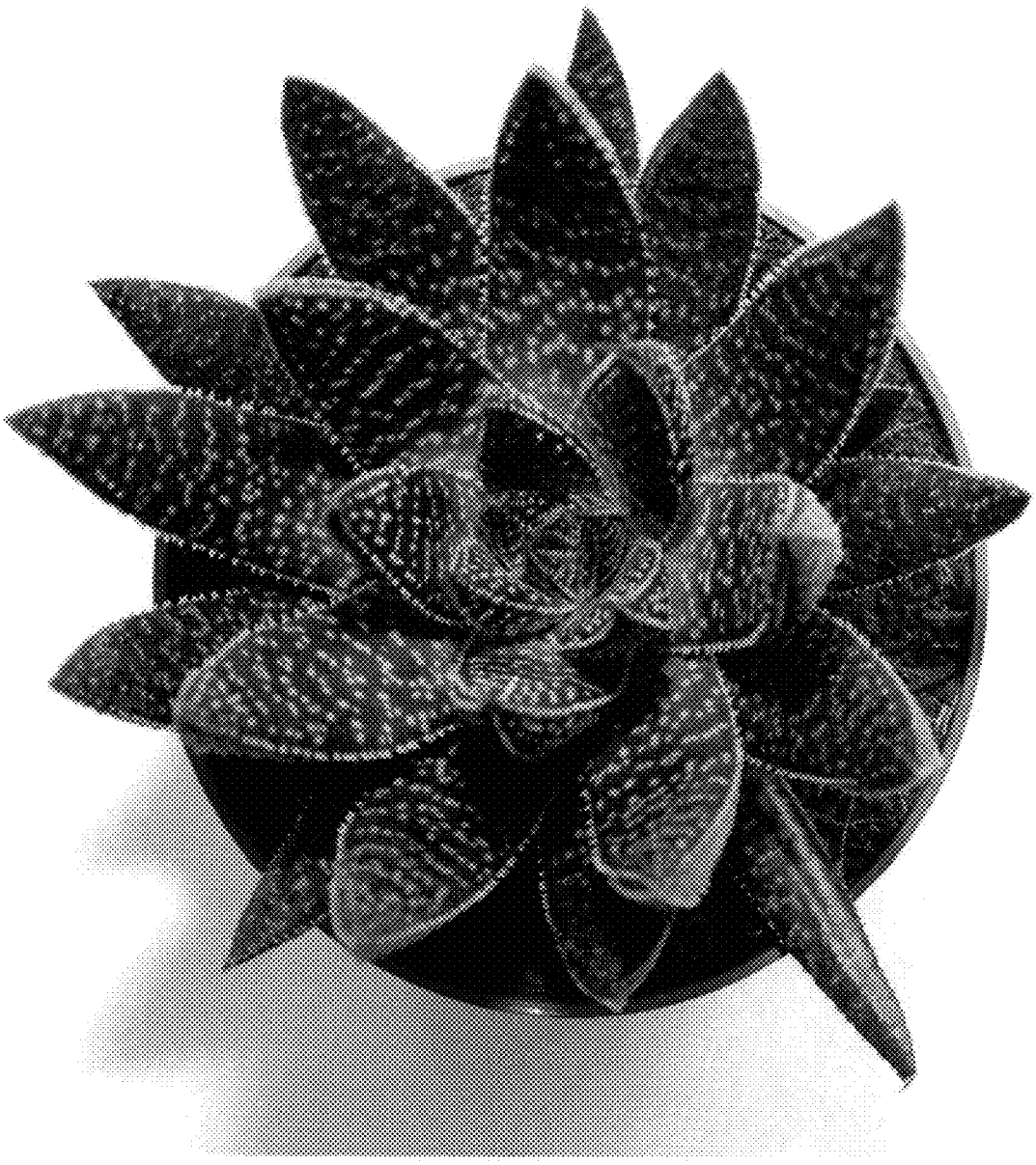
FIG. 2 illustrates, as nearly true as it is reasonably possible to make the same in color photographs of this type, the typical foliage arrangement of 'OVROCKS13'.
Figure 3:
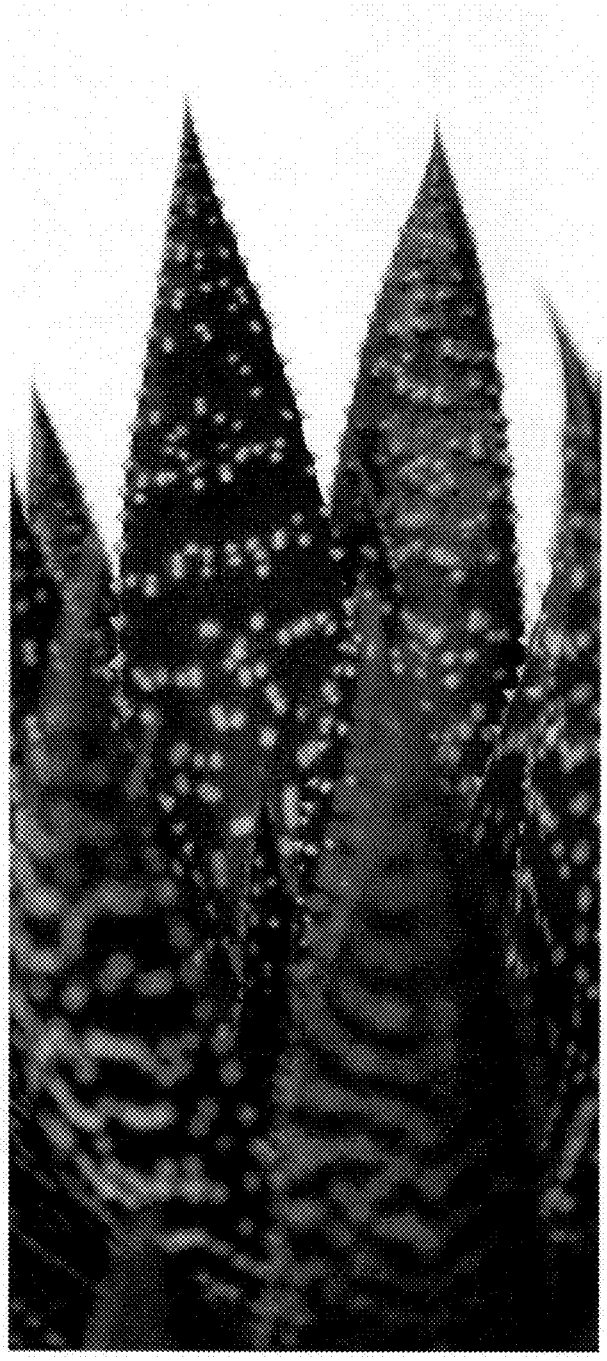
FIG. 3 illustrates, as nearly true as it is reasonably possible to make the same in color photographs of this type, the adaxial surface of the mature foliage 'OVROCKS13'.
Figure 4:
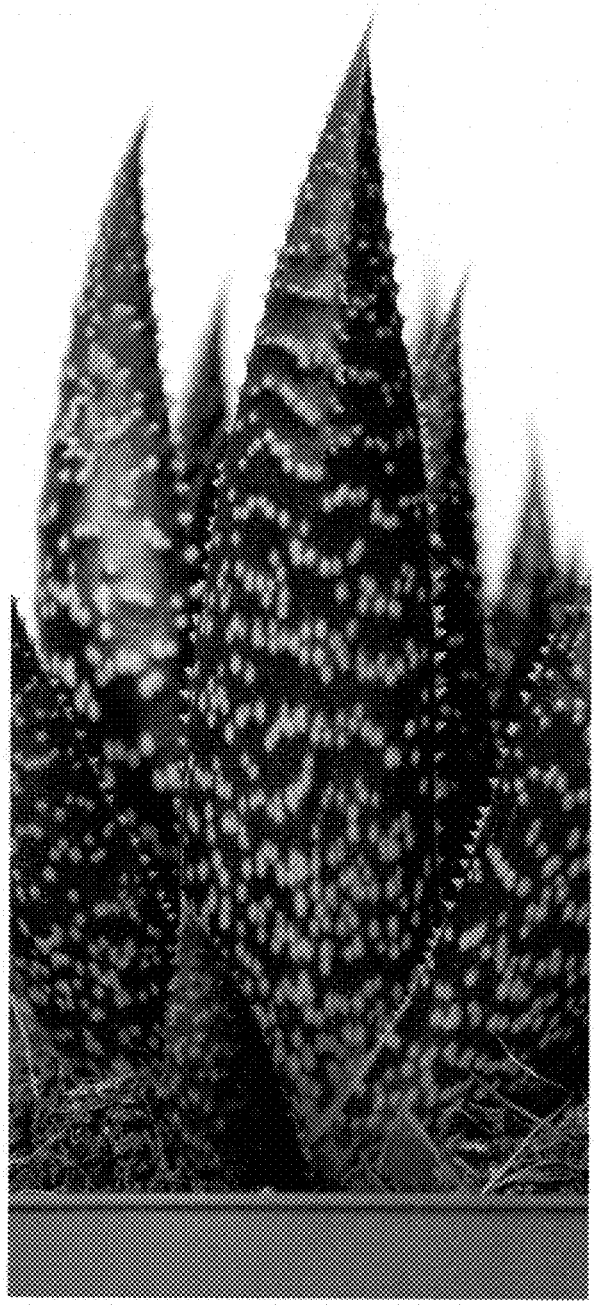
FIG. 4 illustrates, as nearly true as it is reasonably possible to make the same in color photographs of this type, the abaxial surface of the mature foliage 'OVROCKS13'.

The following observations and measurements made in November of 2024 describe averages from a sample set of six specimens of 18 months old 'OVROCKS13' plants grown in 12 cm nursery containers at commercial greenhouse in Heerhugowaard, the Netherlands. Plants were produced using conventional greenhouse production protocols for *Aristeria* which consisted of minimal irrigation and fertilizer applications, and chemical control against common pests and diseases associated with the species as required. Plants were grown under approximately 50 percent shade and no photoperiodic treatments or artificial light was given to the plants.

Those skilled in the art will appreciate that certain characteristics will vary with older or, conversely, with younger plants. 'OVROCKS13' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, Sixth Edition.

A botanical description of 'OVROCKS13' and a comparison with the parent plant, an unnamed x *Aristeria beguinii* (not patented), and the closest known comparator, a *Aristaloe aristata* x *Gasteria carinata* hybrid named 'D Delta' (Community Plant Variety Rights application number 2017/1598) and U.S. Plant Pat. No. 30,905 are provided below.

Plant description:

*Growth habit*.—Succulent perennial with foliage growing in a non-branched basal rosette.

*Plant shape*.—Globular.

*Height from soil level to top of foliar plane*.—11.5 cm.

*Plant spread*.—Average of 12.5 cm.

*Propagation*.—Type — Leaf cuttings and meristematic tissue culture. Time to initiate rooting — Approximately 25 days at 18 degrees Celsius. Crop time — Approximately 18 to 22 weeks to produce a marketable plant in a 12 cm container.

*Disease and pest resistance or susceptibility*.—Neither resistance nor susceptibility to typical *Aristeria beguinii* pests and diseases has been observed.

*Environmental tolerances*.—Adapt to, at least, USDA Zones 10 and temperatures as high as 40 degrees Celsius; low tolerance to rain; high tolerance to wind.

Root system:

*General*.—Fine, well-branched fibrous roots.

Stems:

*Branching habit*.—Leaves in a non-branching basal rosette.

Foliage:

*Arrangement*.—Primary and secondary rosettes forming at the base; an average of 5 secondary basal rosettes form at the base of the main basal rosette.

*Division*.—Simple.

*Attachment*.—Sessile.

*Quantity*.—Approximately 29 leaves per rosette.

*Shape*.—Thick, lanceolate succulent leaves.

*Dimensions*.—10.6 cm long, 2.1 cm wide, and 0.9 cm thick, on average.

*Aspect*.—Slightly concaved.

*Attitude*.—Very erect, inward facing at the inner whorls.

*Apex*.—Narrow acute with a soft mucronate tip.

*Base*.—Broad cuneate.

*Margin*.—Serrulate to dentate; teeth are, on average, 0.8 mm in length and colored greyed-green, nearest to a combination of RHS 193C and 193D, observed in distinct longitudinal rows along the margin.

*Texture, adaxial surface*.—Glabrous and moderately covered with large orbicular protuberances, each approximately 0.2 mm high and 2.0 mm in diameter; protuberances bearing spines near margins and apex.

*Texture, abaxial surface*.—Glabrous and densely covered with prominent protuberances, arranged in axial rows; each papilla approximately 0.2 mm high and 1.0 mm in diameter; protuberances bearing spines near margins, apex, and in a distinct longitudinal row along the midrib.

*Luster, adaxial surface*.—Moderately glossy.

*Luster, abaxial surface*.—Slightly glossy.

*Color*.—Juvenile foliage, adaxial surface — Green, nearest to RHS NN137B, and fading to yellow-green towards the base, nearest to RHS 144B, and tip of the lamina, nearest to 148B and 148C; protuberances are greyed-green, nearest to RHS 192C and 192D. Juvenile foliage, abaxial surface — Green, nearest to RHS NN137A, and fading to yellow-green towards the base, nearest to RHS 144B, and at the tip of the lamina, nearest to RHS 148B and 148C; protuberances are colored in between greyed-green, nearest to RHS 192C and 192D. Mature foliage, adaxial surface — Green to yellow-green, nearest to RHS NN137A and 147A, fading to greyed-green towards the base, nearest to a combination of RHS 194B and 194C, the tip of the lamina appears translucent white, nearest to RHS 155C; protuberances are greyed-green, RHS 193A. Mature foliage, abaxial surface — In between green, RHS NN137A, and yellow-green, RHS 144A, fading lighter towards the base, the tip of the lamina appears translucent white, nearest to RHS 155C; protuberances are colored greyed-green, nearest to RHS 193A.

*Venation*.—No venation is visible.

*Petiole*.—No petiole; leaves are sessile.

Inflorescence: No flowering has been observed to date.

COMPARISONS WITH THE PARENT PLANT

Plants of the new cultivar 'OVROCKS13' differ from the parent, an unnamed x*Aristeria beguinii* (not patented), in the following characteristics described in Table 1 below.

TABLE 1

Comparison Between 'OVROCKS13' And The Parent Plant

| Characteristic | 'OVROCKS13' | The Parent Plant |
|---|---|---|
| Quantity of secondary basal shoots. | Produces an average of five secondary basal shoots. | Produces less than five secondary basal shoots, on average. |
| Foliage arrangement and attitude. | Leaves are more compact than the parent plant. | Leaves are more spread out than 'OVROCKS13' |
| Leaf size. | Leaves are larger than those of the parent plant; broader and longer. | Leaves are smaller than 'OVROCKS13'. |
| Leaf protuberances. | Prominent greyed-green protuberances on the abaxial surface of the mature foliage. | Prominent opaque white protuberances on the abaxial surface of the mature foliage. |

COMPARISONS WITH THE CLOSEST KNOWN COMPARATOR

Plants of the new cultivar 'OVROCKS13' differ from the closest known comparator, a *Aristaloe aristata* x *Gasteria carinata* hybrid named 'D Delta' (Community Plant Variety Rights application number 2017/1598) and U.S. Plant Pat. No. 30,905, in the following characteristics described in Table 2 below.

TABLE 2

Comparison Between 'OVROCKS13' And 'D Delta'

| Characteristic | 'OVROCKS13' | 'D Delta' |
|---|---|---|
| Leaf shape and size. | 'OVROCKS13' has thicker lanceolate leaves that are larger than 'D Delta'. | Leaves are smaller and thinner than 'OVROCKS13'. |
| Growth habit. | More compact with less space between leaves than 'D Delta'. | Branching in a broader habit than 'OVROCKS13'. |
| Leaf attitude. | Very erect to slightly inward facing. | Erect to slightly outward facing. |

That which is claimed is:

1. A new and distinct variety of x*Aristeria beguinii* plant named 'OVROCKS13', substantially as described and illustrated herein.

* * * * *